United States Patent [19]

Berry, Jr.

[11] Patent Number: 4,767,995

[45] Date of Patent: Aug. 30, 1988

[54] CONDUCTIVITY CELL WITH ADJUSTABLE CONCENTRIC ELECTRODES

[76] Inventor: William J. Berry, Jr., Post Office Box 2993, Durham, N.C. 27705

[21] Appl. No.: 940,347

[22] Filed: Dec. 11, 1986

[51] Int. Cl.$^4$ .............................................. G01N 27/07
[52] U.S. Cl. ..................... 324/447; 204/409; 324/441; 324/448; 324/450
[58] Field of Search ............... 324/446, 447, 448, 449, 324/450, 438, 439, 62 R, 441; 204/409

[56] References Cited

U.S. PATENT DOCUMENTS

| | | | |
|---|---|---|---|
| 2,376,694 | 5/1945 | Hewlett | 324/447 X |
| 2,611,007 | 9/1952 | Cade et al. | 324/441 |
| 3,808,523 | 4/1974 | Jobe | 324/446 |

*Primary Examiner*—Reinhard J. Eisenzopf
*Assistant Examiner*—Robert W. Mueller

[57] ABSTRACT

A conductivity cell is presented having a solid inner electrode and a hollow electrode whereby the inner electrode is adjustably mounted. The adjustable feature allows the cell to be accurately calibrated for various fluids having a wide range of conductivities.

5 Claims, 1 Drawing Sheet

CONDUCTIVITY CELL WITH ADJUSTABLE CONCENTRIC ELECTRODES

BACKGROUND OF THE INVENTION

1. Field of the Invention

The invention contained herein relates to conductivity cells of the flow-through type having inner and outer electrodes for measuring the conductivity of fluids passing therebetween.

2. Description of the Prior Art and Objectives of the Invention

Various electrolytic conductivity cells have been conceived in the past such as set forth in U.S. Pat. No. 3,916,300 and instruments termed SOLU-BRIDGE® made by Beckman Instruments, Inc. These devices are useful in determining the conductivity of fluids such as water and are generally designed for a specific conductivity range. With manufacturers becoming increasing aware of problems associated with impure water, more and more attention is being paid to purity and as a result conductivity is being measured more often and in various stages of manufacturing processes and in raw materials. Since fluids such as water vary greatly in their conductivity, it is not uncommon for a manufacturer to maintain an inventory of conductivity cells, each for a different range of conductivity measurement.

With this background known of conventional conductivity measuring devices, the present invention was conceived and one of its objectives is to provide a conductivity cell which has an adjustable inner electrode to provide a wide range of conductivity measurements.

It is another objective of the present invention to provide a conductivity cell which is relatively simple in construction and economical to manufacturer.

It is still another objective of the present invention to provide a conductivity cell which can be simply adjusted and calibrated by a technician with little training.

Various other objectives and advantages of the present invention will become apparent to those skilled in the art as a more detailed explanation of the invention is presented below.

SUMMARY OF THE INVENTION

The aforesaid and other objectives are met by forming a conductivity cell with a housing of durable plastic such as polyvinyl chloride (PVC), polyproplyene, or other generally stable, inert plastics. Included within the housing is a cylindrical, hollow titanium alloy outer electrode and an inner, solid titanium alloy electrode which is threadably mounted with the housing. By turning a control knob positioned on the exterior portion of the inner electrode, the inner electrode can be adjustably extended into or withdrawn from the center of the hollow outer electrode thereby providing more or less surface area within the outer electrode for conductivity. A meter is connected to the inner and outer electrodes and to a temperature sensor positioned in the passageway between the electrodes for conductivity determinations.

DESCRIPTION OF THE PREFERRED EMBODIMENT

Figure 1:
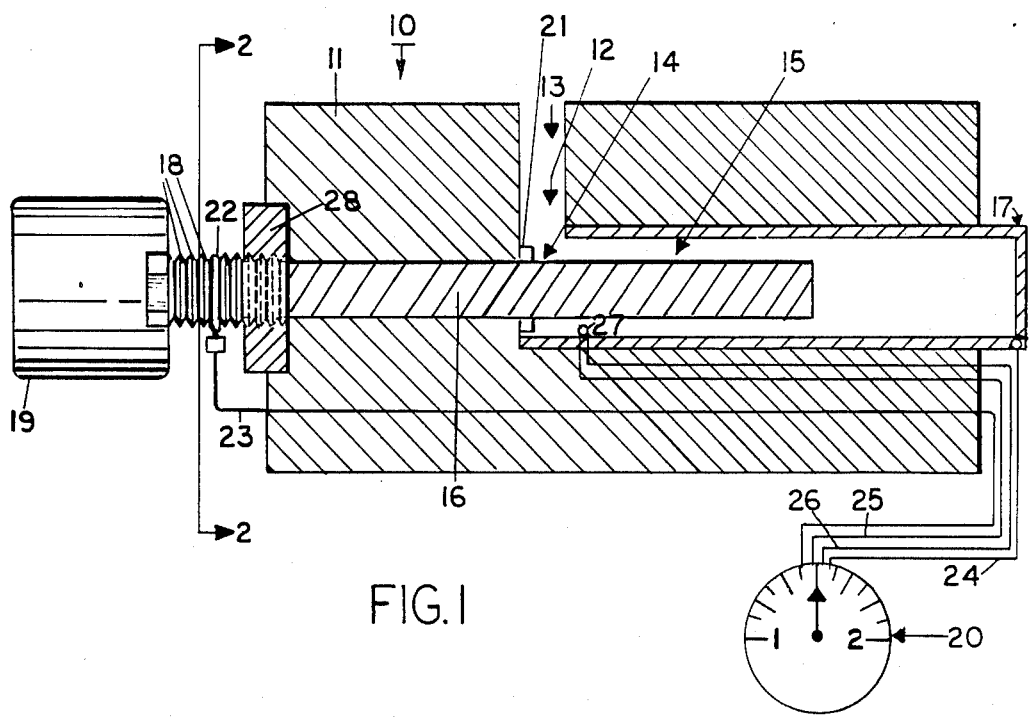
FIG. 1 is a cross-sectional view of the conductivity cell of the present invention with a conductivity meter attached thereto.

The preferred form of the invention is shown in FIG. 1 and includes a housing formed from PVC and having an outer electrode formed from a titanium alloy. The inner electrode is also formed from a titanium alloy and is adjustably threaded into the housing. A knob on the exterior end of the inner electrode allows the user to adjust the conductivity measurement range by rotatably extending or withdrawing the inner electrode. A circuit in the housing allows the flow of fluid into the passageway between the inner and outer electrodes. A meter is slidably attached to the exterior end of inner electrode and is joined to the outer electrode and to a temperature sensor which provides a temperature compensation for the meter.

DETAILED DESCRIPTION OF THE DRAWINGS

Turning now to the drawings, conductivity cell 10 as shown in FIG. 1 includes an outer housing 11 which may be formed from suitable plastic such as PVC or polypropylene. Conduit 12 has an inlet 13 whereby a hose, a fitting or otherwise can be mounted to allow fluids to enter conduit 12 and to flow through outlet 14 and into passageway 15 between inner electrode 16 and outer electrode 17. As shown on the exterior portion of inner electrode 16, are a series of threads 18 which provide adjustment as knob 19 is rotated. Seal 21 is positioned to prevent fluid leakage along the unexposed portion of inner electrode 16.

Meter 20 depicted in FIG. 1 is of the conventional wheatstone bridge type having a gauge on its face with graduations for relative conductivity measurements. As is understood, conductivity of water is generally expressed in micromhos-per-centimeter whereby a mho is defined as a reciprocal of an ohm. In water and other such fluids, the higher the resistance, the lower its reciprocal, conductivity. With increasing demands for higher and higher purity water, 10 to 20 megohm water is not uncommon and this means water with a total dissolved solids content on the order of 0.01 to 0.02 parts per million.

By using standarized solutions, conductivity cell 10 can be adjusted and calibrated to display a conductivity range of 100–200 mmho (micro mho) water or can be further adjusted to demonstrate 10–20 mmho water on its guage. Additional ranges can be calibrated by making the proper adjustment in the relative position of inner electrode 16 and outer electrode 17 and with the use of a properly calibrated fluid. As would be understood once conductivity cell 10 is calibrated then water of an unknown conductivity is tested and its conductivity is determined.

As further shown in FIG. 1, connector slide 22 is attached to the exterior portion of inner electrode 16 and is joined to meter 20 through connector line 23. Connector line 24 provides an electrical signal between outer electrode 17 and meter 20 whereas connector lines 25 and 26 join temperature sensing means 27 to meter 20, which as previous mentioned contains conventional wheatstone bridge circuitry having temperature compensation. Temperature sensing means 27 may consist of a thermoprobe, thermistor, thermometer or a thermal junction. It has been found that by placing the temperature sensing means in contact with the actual fluid to be tested, an accurate and reliable temperature compensation for the conductivity reading is assured and the temperature sensing is both fast and efficient.

Figure 2:
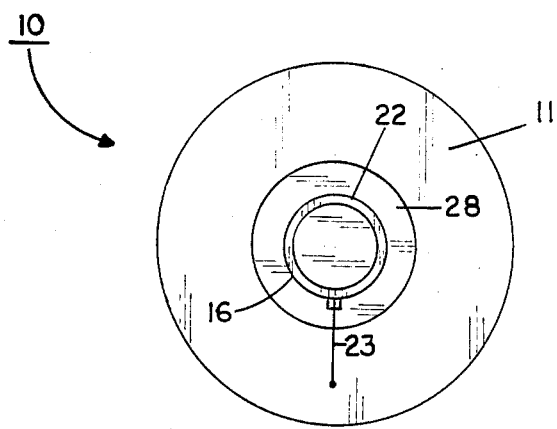
FIG. 2 is an end view along lines 2—2 expanded and shown in elevational fashion.

FIG. 2 shows an end view of conductivity cell 10 shown along line 2—2 of FIG. 1 but as a full end elevational view demonstrating bearing 28 which is rigidly affixed to housing 11.

The illustrations and examples presented herein are for demonstrative purposes and are not intended to limit the scope of the appended claims.

I claim:

1. A conductivity cell comprising: a solid, unitary inner electrode and an outer electrode, said outer electrode surrounding said inner electrode, a fluid passageway, said passageway formed between said inner and outer electrodes for directing fluid between, a conduit, said conduit having a fluid inlet and a fluid outlet, said conduit in communication with said passageway, temperature sensing means, said sensing means positioned within said passageway between said electrodes to respond to fluids therein, said inner electrode adjustably mounted within said outer electrode, a meter, said meter communicating with said sensing means and with said inner and outer electrodes, said meter to provide conductivity values of fluid within said conduit.

2. A conductivity cell as claimed in claim 1 wherein said inner electrode is threadably adjustable within said outer electrode.

3. A conductivity cell as claimed in claim 1 wherein said meter is slidably attached to said inner electrode.

4. A conductivity cell comprising: a housing, a conduit within said housing, a hollow outer electrode, said outer electrode mounted in said housing, an inner electrode, said inner electrode positioned in said housing and extending into said outer electrode, said outer and said inner electrodes forming a fluid passageway therebetween, temperature sensing means, said sensing means positioned between said electrodes in said passageway, said conduit communicating with said passageway, said inner electrode adjustably mounted in said housing whereby said inner electrode can be adjustably extended into said outer electrode.

5. A conductivity cell as claimed in claim 4 and including a meter, said meter communicating with said inner and outer electrodes and with said temperature sensing means for providing conductivity readings of fluid within said passageway.

* * * * *